United States Patent [19]

Robinson et al.

[11] Patent Number: 4,717,768

[45] Date of Patent: Jan. 5, 1988

[54] PROCESS FOR SEPARATION OF SYN AND ANTI OXIME ISOMERS OF CEPHALOSPORIN-COMPOUNDS

[75] Inventors: Colin Robinson, Allinthwaite; David T. Eastlick, Grange-over-Sands; Audrey J. Bownass, Haverthwaite, all of England

[73] Assignee: Glaxo Group Limited, London, England

[21] Appl. No.: 648,382

[22] Filed: Sep. 7, 1984

[30] Foreign Application Priority Data

Sep. 9, 1983 [GB] United Kingdom ............... 8324152

[51] Int. Cl.$^4$ .................. C07D 501/12; A61K 31/545
[52] U.S. Cl. .................................... 540/222; 540/224; 540/225; 540/227; 540/228; 540/230
[58] Field of Search ................... 544/20; 540/228, 230, 540/225, 222, 224, 227

[56] References Cited

U.S. PATENT DOCUMENTS 4,028,355  6/1977  Blackburn ............................. 544/20
4,145,539  3/1979  Hattori et al. ........................ 544/20
4,339,390  7/1982  Ali et al. .......................... 260/397.45
4,399,274  8/1983  Goegelman et al. ................. 536/7.1

FOREIGN PATENT DOCUMENTS 7018688  1/1982  Japan ..................................... 544/20
1441897  of 0000  United Kingdom .

OTHER PUBLICATIONS

O'Connor, "Macroreticular Resin Chromatography of Antibiotics", Methods Enzymole, 1975, 43, 296–299.
Yamato et al., "Extraction of Benzene Hexachloride Isomers . . . ", Chem. Abst., 90; 12040 (j), (1979).
Ho et al., "Synthesis of New Macroreticular Absorbents . . . ", Chem. Abst., 95:225612 (n), 1981.
Axelson et al., "Separation and Configuration of Syn and Anti Isomers of Testosterone Oximes", Chem. Abst., 89:110096 (f).
Kurita et al., J.A.C.S. 98 (10), 3023–3025.
J. Antibiotics 29 (11), 1243–1245.
J. Assoc. Off. Anal. Chem., (vol. 61, No. 5, 1978), pp. 1135–1139.

Primary Examiner—Nicholas S. Rizzo
Attorney, Agent, or Firm—Bacon & Thomas

[57] ABSTRACT

A process for the separation of a mixture of syn and anti oxime isomers one from the other which comprises adsorbing said mixed oxime isomers onto a non-functional macroreticular adsorption resin, and eluting said resin to yield at least one eluate fraction containing one of said isomers while being substantially free of the other of said isomers.

The application of this process to the separation of syn and anti isomers of cephalosporin compounds possessing an oxime grouping in a side-chain in the 7$\beta$-position, and of acids corresponding to this 7$\beta$-side chain, is described.

20 Claims, No Drawings

PROCESS FOR SEPARATION OF SYN AND ANTI OXIME ISOMERS OF CEPHALOSPORIN-COMPOUNDS

This invention relates to a novel process for the separation of geometrical isomers of chemical compounds, and more particularly for the separation of geometrical isomers of oxime group-containing compounds.

Many types of oxime group-containing compounds, that is, compounds containing a group of formula

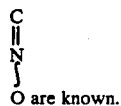

are known.

Especially important are cephalosporin compounds possessing an oxime grouping in a side chain in the 7β-position, preferably a side-chain having the formula

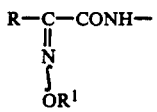

(where R and $R^1$ independently represent a hydrogen atom or an organic group) and the carboxylic acids used in the formation of such side-chains.

Thus, particularly valuable oxime compounds are carboxylic acids of the formula

(where R and $R^1$ have the above meanings and $R^2$ is a hydroxy group or the residue of a 7-aminocephem-4-carboxylic acid) and derivatives thereof.

The most important of the above cephalosporin oxime compounds may be defined by the formula

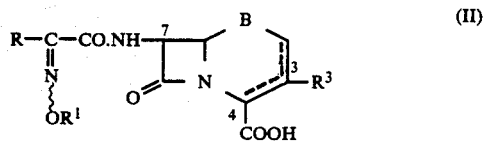

where each of R, $R^1$ and $R^3$ independently represents a hydrogen atom or an organic group, B is —S— or >S→O (α- or β-), and the dotted line indicates $\Delta^2$ or $\Delta^3$ unsaturation.

If any of R, $R^1$ or $R^3$ comprises a positively charged grouping, the compound of formula I or II may exist in the form of an internal salt formed between the said positively charged group and a carboxylate group —COO$^\ominus$ at the 4-position of the cephem nucleus.

It will be appreciated that alternative configurations of the oxime group in the above formulae I and II result in geometrical isomerism. Thus, compounds having the configuration

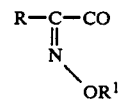

are designated syn-isomers, whilst compounds having the configuration

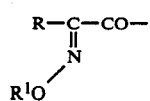

are designated anti-isomers.

Cephalosporin compounds possessing an oxime group in the 7β-side chain have generally been found to exhibit high stability to β-lactamases produced by many pathogenic organisms. However, it has been found that the syn-isomers of these cephalosporin compounds exhibit superior antibacterial activity to the corresponding anti-isomers, so that the oxime group-containing cephalosporin antibiotics are generally obtained and used in the form of their syn-isomers. The syn-isomers of the cephalosporin compounds may be prepared by employing an acid of formula I (where $R^2$ is a hydroxy group) substantially in the syn-isomer form, or a derivative thereof, in the 7-side chain coupling reaction and controlling the reaction conditions in this and any subsequent steps to avoid isomerisation to the anti-isomer. However, in some circumstances mixtures of syn and anti-isomers are formed and it is then necessary to separate them.

The separation of syn and anti-isomers of oxime compounds by chromatography on silica gel is known. For example, British Patent Specification No. 1,576,625 describes the separation of syn and anti-isomers of compounds of formula I or derivatives thereof by this method. However, the separation achieved by this method depends to a large extent on the solvent system employed to elute the isomers and the separation of isomers of different compounds often require quite different solvent systems. In general, such a procedure is not suitable for large scale operation.

A further method known in the art for the separation of syn and anti-isomers of oxime compounds is fractional crystallisation whereby one of the isomers is crystallised from a solution of the mixed isomers while the other isomer is left in solution. However, it has been found that this technique does not achieve satisfactory separation of isomers of cephalosporin compounds.

Non-functional macroreticular adsorption resins have found application in the purification of chemical compounds, for example in processes where a cephalosporin compound is separated from other components of a fermentation or reaction solution by loading the mixture onto the resin, washing to remove undesired components and eluting the desired compound. Thus, for example, the isolation of cephalosporin C from a fermentation solution using non-functional macroreticular adsorption resins is described in British Patent Specification No. 1,303,728. Similarly, the purification of semisynthetic cephalosporin compounds on such resins is exemplified, for example, in British Patent Specification Nos. 1,600,735, 1,581,854 and 2,036,738 A. However, there is no indication in this prior art that non-functional macroreticular adsorption resins may be used to separate geometrical isomers.

We have now surprisingly found that the geometrical isomers of oxime group-containing compounds can be separated one from the other with high efficiency using aqueous elution from non-functional macroreticular adsorption resins.

Thus, in one aspect the invention provides a process for the separation of a mixture of syn and anti-oxime isomers one from the other which comprises adsorbing said mixed oximes onto a non-functional macroreticular adsorption resin, and eluting said resin to yield at least one eluate fraction containing one of said isomers substantially free of the other.

In general, for efficient separation it is preferred that the oxime isomers should be in aqueous media, thus enabling their elution from the resin using aqueous eluants. In general, the solubility of the isomers in pure water at ambient temperature is desirably at least 0.1% by weight, more preferably at least 5%.

The aqueous eluant may conveniently be water or aqueous solutions containing salts and/or water-miscible organic solvents. Water is the preferred eluant. In general, such solutions may contain up to about 85% by volume of organic solvent but this figure may if desired be exceeded depending on the particular compounds to be separated. Solvent will normally be used to enhance the solubility of the oxume isomers in the eluant. In general, more efficient separation is to be expected if the quantity of solvent is close to the minimum required to provide sufficient solubility for elution from the resin. Examples of salts include those derived from acids such as formic, chloroacetic or acetic acid, with for example an alkali metal cation such as sodium or potassium. Examples of organic solvents include alcohols, e.g. methanol or isopropanol, or ketones e.g. acetone. The mixed isomers may be loaded onto the resin in solution. This solution will generally be an aqueous solution but solutions in organic solvents may also be used.

A solution containing the isomers to be separated may be brought into contact with the non-functional macroreticular adsorption resin in any desired way, most suitably by loading it onto a column or bed of granular resin e.g. in conventional bead form.

Where the resin is used in the form of a column, the separation according to the invention may be essentially chromatographic. Thus, elution will tend to separate the isomers into bands which may be eluted as separate peaks. In our experience, the desired syn-isomers surprisingly always elute first, which is particularly advantageous in practice.

The peaks containing the individual isomers may be eluted separately, in which case the syn isomer obtained will contain little or none of the anti isomers. However, more typically, the peaks will overlap slightly so that after initial fractions containing only syn isomer, fractions will be eluted which contain more and more of the anti isomer in addition to the syn isomer. It will be appreciated that if all such 'mixed' fractions are rejected, the syn isomer isolated from the preceding fractions will be of high purity with respect to the anti isomer, but there may be considerable losses of desired syn isomers. On the other hand, overall recovery of syn isomers can be increased in such circumstances, if fractions are also collected which contain small quantities of the anti isomer from the overlapping peak. The operator thus has the option, where the peaks overlap, of recovering syn isomers of very high purity but in reduced yield or at reduced purity with respect to anti-isomer but higher yield. However, in either case, the process of the invention enables the syn isomer to be obtained substantially free from the anti isomer, i.e. free from anti isomer within the tolerance acceptable for the intended use of the product. Where the oxime is a final pharmaceutical product, the percentage of anti isomer present is preferably not more than 3% by weight, more preferably not more than 1.5%. Where the oxime is an intermediate, however, somewhat higher levels of anti-isomer may be acceptable, e.g. up to 5% by weight, depending on the intended further processing of the intermediate.

The eluate fraction collected may, if desired, be reapplied to the resin to effect further purification. It may be desirable to concentrate such an eluate fraction prior to re-application.

Elution of the isomers from the non-functional macroreticular resin may be monitored by conventional techniques, such as high performance liquid chromatography (HPLC).

The separated isomers may be isolated from the eluate fraction(s) containing them by conventional techniques such as by solvent extraction and/or crystallisation.

Non-functional macroreticular adsorption resins which may conveniently be employed according to the invention typically have a surface area of from 100 to 1300 $m^2.g^{-1}$, e.g. 140–950 $m^2.g^{-1}$, and an average pore diameter of from 2–18 nm, e.g. 3–15 nm. The resin may be, for example, a copolymer of styrene cross-linked with divinylbenzene, examples of such resins which may be used include Amberlite XAD-2 and XAD-1180 (Rohm and Haas), Diaion HP-20 and HP-21, and SP207 (Mitsubishi), Duolite S-861 and S-8602 (Rohm and Haas), and Kastell-S112 (Montedison). Other suitable resins include acrylic ester polymers such as XAD-7 and XAD-8 of Rohm & Haas. The resins may be regenerated by conventional means and re-used.

According to a preferred feature, the invention provides a process as defined above for the separation of syn and anti oxime isomers of compounds of formula (I) and derivatives thereof. Important cephalosporin compounds of formula (I) are those of formula (II) as defined above. In formula II, B is preferably —S— and the unsaturation represented by the dotted line is preferably $\Delta^3$.

The group R in the above formulae represents, as indicated above, a hydrogen atom or an organic group. Thus, for example, R may be selected from carbocyclic groups preferably containing 5–12 atoms and heterocyclic groups; these are preferably unsaturated or aromatic and the heterocyclic group preferably possess 5 or 6 ring members and contain from 1 to 4 heteroatoms selected from sulphur, nitrogen and oxygen; the above groups may be substituted, for example by one or more halogen atoms or by amino or hydroxy groups, which may be in protected form, or alkoxy groups. R may also represent a $C_{1-6}$ alkyl group which may be substituted, for example, by oxo and/or halogen. Examples of such groups include phenyl, thienyl, furyl, aminothiazolyl and aminothiadiazolyl groups.

Of particular importance are compounds in which R represents a fur-2-yl group or a protected or unprotected 2-aminothiazol-4-yl group.

The group $R^1$ in the above formulae represents, as indicated above, a hydrogen atom or an organic group. When $R^1$ represents an organic group this will desirably be an etherifying monovalent organic group containing up to 16 carbon atoms and linked to the oxygen atom through a carbon atom.

Thus, for example, $R^1$ may be a hydrogen atom or an aliphatic group such as $C_{1-6}$ alkyl, $C_{3-7}$ cycloalkyl, $C_{4-10}$ cycloalkylalkyl, $C_{2-6}$ alkenyl or $C_{4-7}$ cycloalkenyl, or a $C_{5-10}$ aryl (e.g. phenyl) or $C_{5-10}$ aralkyl (e.g. benzyl) group, wherein any of the above groups may be optionally substituted by a halogen atom or a free or blocked carboxy (e.g. lower alkoxycarbonyl) group, or by a carbamoyl, cyano or protected or unprotected amino group.

There may particularly be mentioned compounds in which $R^1$ represents a methyl group, a free or blocked 2-carboxyprop-2-oxy group or a cyclopropylmethyl group.

The group $R^3$ in the above formula II represents, as indicated above, a hydrogen atom or an organic group. When $R^3$ represents an organic group, this may be a saturated or unsaturated, substituted or unsubstituted, organic group containing 1-20 carbon atoms. Important saturated organic groups include methyl and ethyl; important unsaturated organic groups include vinyl and substituted vinyl groups.

Particularly important meanings for $R^3$ in the above formula II include a hydrogen atom; a vinyl group substituted by a heterocyclicthio group in which the heterocyclic portion comprises a 5- or 6-membered ring containing up to four nitrogen atoms and optionally one sulphur atom and substituted by one or more groups independently selected from methyl, protected or unprotected oxo, formylmethyl, protected or unprotected hydroxy and free or blocked carboxymethyl groups; or a group of formula $$-CH_2Y$$

(wherein Y represents a halogen atom, a hydroxy, acyloxy or carbamoyloxy group or the residue of a pyridine base e.g. of pyridine, 2,3-cyclopentenopyridine, nicotinamide or isonicotinamide or of a heterocyclicthiol comprising a 5- or 6-membered heterocyclic portion containing up to four nitrogen atoms and optionally one sulphur atom and substituted by one or more, e.g. 1 to 3, groups independently selected from methyl, protected or unprotected oxo, formylmethyl, carbamoylmethyl, protected or unprotected hydroxy and free or blocked carboxymethyl groups).

The oxime isomers may also be derivatives of the compounds of formula I. The carboxyl group formed when $R^2$ is a hydroxy group, or the 4-carboxy group of a 7-aminocephem-4-carboxylic acid residue, may thus be present in the free acid form, as in the form of a salt with a base or in the form of a blocked carbonyl function such as an ester or amide grouping or a metabolically labile ester grouping. Such blocked carboxyl functions may thus be ester groups having 1-12 carbon atoms in the esterifying group, e.g. t-butyl or diphenylmethyl groups. Metabolically labile ester groups include, for example, acyloxyalkyl groups, such as an acetoxyethyl group.

As indicated above, it is preferred that the oxime isomers are soluble in aqueous eluants. In general, there will be at least one hydrophilic grouping in the molecule, e.g. a salt-forming grouping such as a carboxyl or amino group or a quaternary ammonium group such as a pyridinium group.

It should be appreciated that protecting groups are commonly employed in the cephalosporin art to protect any sensitive groups in the molecule in question to avoid undesirable side reactions. Thus, for example, amino, hydroxy, carboxy or oxo groups may be protected using known protecting groups by conventional methods. Thus, for example an amino group may be protected by tritylation, acylation (e.g. chloroacetylation or formylation) or protonation. Suitable protecting groups and techniques are fully described in text books such as "Protective Groups in Organic Chemistry" Ed. J. F. W. McOmie, Plenum Press (1973), or "Protective Groups in Organic Synthesis" by T. W. Greene, Wiley Interscience (1981). Any protecting groups may thereafter be removed in any convenient way which does not cause breakdown of the desired compound. Such groups may thus in some cases be present at the stage of cephalosporin synthesis at which the separation according to the invention is effected.

It will be appreciated that various tautomeric and isomeric (e.g. optical, geometric or structural isomeric) forms of any of the above groups or compounds may exist, and the definitions given herein include within their scope where appropriate all such tautomeric and isomeric forms.

Examples of cephalosporin antibiotics whose isomers may be separated by the process of the present invention include particularly the compounds cefuroxime: (6R,7R)-7-[(Z)-2-(fur-2-yl)-2-methoxyiminoacetamido]-3-carbamoyloxymethylceph-3-em-4-carboxylic acid and the 3-acetoxymethyl and 3-hydroxymethyl analogues thereof;

ceftazidime: (6R,7R)-7-[(Z)-2-(2-aminothiazol-4-yl)-2-(2-carboxyprop-2-oxyimino)acetamido]-3-(1-pyridiniummethyl)ceph-3-em-4-carboxylate;

ceftizoxime: (6R,7R)-7-[(Z)-2-(2-aminothiazol-4-yl)-2-methoxyiminoacetamido]-ceph-3-em-4-carboxylic acid;

ceftriaxone: (6R,7R)-7-[(Z)-2-(2-aminothiazol-4-yl)-2-methoxyiminoacetamido]-3-[(2,5-dihydro-6-hydroxy-2-methyl-5-oxo-as-triazin-3-yl)thiomethyl]-ceph-3-em-4-carboxylic acid disodium salt;

cefotaxime: (6R,7R)-3-acetoxymethyl-7-[(Z)-2-(2-aminothiazol-4-yl)-2-methoxyiminoacetamido]ceph-3-em-4-carboxylic acid;

cefmenoxime: (6R,7R)-7-[(Z)-2-(2-aminothiazol-4-yl)-2-methoxyiminoacetamido]-3-[(1-methyl-1H-tetrazol-5-yl)thiomethyl]ceph-3-em-4-carboxylic acid;

cefodizime: (6R,7R)-7-[(Z)-2-(2-aminothiazol-4-yl)-2-methoxyiminoacetamido]-3-[(5-carboxymethyl-4-methyl-1,3-thiazol-2-yl)thiomethyl]ceph-3-em-4-carboxylic acid;

(6R,7R)-7-[(Z)-2-(2-aminothiazol-4-yl)-2-methoxyiminoacetamido]-3-[2-(5,6-dioxo-4-formylmethyl-1,4,5,6-tetrahydro-1,2,4-triazin-3-yl)thiovinyl]ceph-3-em-4-carboxylic acid;

(6R,7R)-7-[(Z)-2-(2-aminothiazol-4-yl)-2-(carboxymethoxyimino)acetamido]-3-vinyl-ceph-3-em-4-carboxylic acid;

cefpirome: (6R,7R)-7-[(Z)-2-(2-aminothiazol-4-yl)-2-methoxyiminoacetamido]-3-[(2,3-cyclopentenopyridinium)methyl ceph-3-em-4-carboxylate;

(6R,7R)-7-[(Z)-2-(2-aminothiazol-4-yl)-2-cyclopropylmethoxyiminoacetamido]-3-pyridiniummethyl-ceph-3-em-4-carboxylate; and (6R,7R)-7-[(Z)-2-(2-aminothiazol-4-yl)-2-methoxyiminoacetamido]-3-[(1-methyl-1-pyrrolidinium)methyl]-ceph-3-em-4-carboxylate.

Salts of the compounds of formula I which may be used, include:

(a) inorganic base salts such as ammonium, alkali metal (e.g. potassium and sodium) or alkaline earth metal (e.g. calcium) salts, amino acid salts (e.g. lysine and arginine salts), and organic base salts such as procaine, phenylethylbenzylamine, dibenzylethylenediamine, ethanolamine, diethanolamine and N-methylglucosamine salts, and (b) acid addition salts formed with, for example, hydrochloric, hydrobromic, sulphuric, nitric, phosphoric, formic, trifluoroacetic, p-toluenesulphonic and methanesulphonic acids.

Important solvates include the hydrates.

The process according to the invention thus enables the efficient and simple separation of geometrical isomers of oxime group-containing compounds to be achieved by a method capable of large-scale operation.

The following Examples serve to illustrate the invention. All temperatures are in °C.

EXAMPLE 1

Separation of isomers of Sodium (6R,7R)-3-carbamoyloxymethyl-7-[2-(fur-2-yl)-2-methoxyiminoacetamido]ceph-3-em-4-carboxylate A mixture of sodium (6R,7R)-3-carbamoyloxymethyl-7-[2-(fur-2-yl)-2-methoxyiminoacetamido]ceph-3-em-4-carboxylate, syn-isomer (27.81 g) (added as the tetrahydrofuran solvate) and its corresponding anti-isomer (6.03 g) was dissolved in water (300 ml). The solution was loaded at 500 ml/hour on a column containing Amberlite XAD-1180 resin (500 ml). All the cephalosporin was retained on the resin, none being detected in the percolate, which was discarded. The resin was then eluted with water at 500 ml/hour and the eluate collected in fractions. Each fraction was examined using HPLC for the presence of the syn and anti-isomers. The early eluate fractions were combined together (total volume 750 ml); methyl acetate (750 ml) and sodium chloride (150 g) were added with stirring. Whilst continuing stirring, 15% v/v sulphuric acid was added to pH 2.0. After stirring for a further 10 minutes at pH 2.0, the lower aqueous phase was separated and extracted with a second portion of methyl acetate (100 ml). The methyl acetate fractions were combined and sodium 2-ethylhexanoate solution was added to pH 5.5. The resultant slurry was filtered. The filter cake was washed with methyl acetate and dried overnight in vacuo at 40°. The dry product (24.33 g) was found to contain 22.0 g of sodium (6R,7R)-3-carbamoyloxymethyl-7-[2-(fur-2-yl)-2-methoxyiminoacetamido]ceph-3-em-4-carboxylate, syn-isomer and 0.1 g of the corresponding anti isomer.

EXAMPLE 2

Separation of isomers of (6R,7R)-7-[2-(fur-2-yl)-2-methoxyiminoacetamido]-3-hydroxymethylceph-3-em-4-carboxylic acid.

A sample of (6R,7R)-7-[2-(fur-2-yl)-2-methoxyiminoacetamido]-3-hydroxymethylceph-3-em-4-carboxylic acid containing the syn isomer (33.2 g) and the anti isomer (3.72 g) was dissolved in water (about 500 ml) by adding sodium bicarbonate to pH 7.0 with stirring. The hazy solution was filtered and adjusted to pH 5.0 using sulphuric acid. This solution (about 600 ml) was loaded at 500 ml/hour on a column containing Amberlite XAD-1180 resin (500 ml). All the cephalosporin was retained on the resin, none being detected in the percolate, which was discarded. The resin was eluted with water at 500 ml/hour and the eluate collected in fractions. Each fraction was examined using HPLC for the presence of the syn and anti isomers. The early eluate fractions were combined together (total volume 1300 ml) and cooled with stirring to 5°. Ethyl acetate (108 ml) was added followed by 20% v/v sulphuric acid to pH 2.3. The resulting slurry was stirred at 50 for 40 minutes, filtered, washed with chilled water (6×50 ml) and transferred to an open tray for drying overnight in vacuo at 40°. The dry product (28.38 g) was found to contain 28.01 g of (6R,7R)-7-[2-(fur-2-yl)-2-methoxyiminoacetamido]-3-hydroxymethylceph-3-em-4-carboxylic acid, syn isomer and 0.09 g of the corresponding anti isomer.

EXAMPLE 3

Separation of Isomers of sodium (6R,7R)-3-carbamoyloxymethyl-7-[2-(fur-2-yl)-2-methoxyiminoacetamido]ceph-3-em-4-carboxylate.

A mixture of sodium (6R,7R)-3-carbamoyloxymethyl-7-[2-(fur-2-yl)-2-methoxyiminoacetamido]ceph-3-em-4-carboxylate, syn isomer (27.81 g) and the corresponding anti isomer (6.03 g) (added as the tetrahydrofuran solvate) was dissolved in water (300 ml). The solution was loaded at 500 ml/hour on a column containing Diaion HP-20 resin (500 ml). All the cephalosporin was retained on the resin, none being detected in the percolate, which was discarded. The resin was eluted with water at 500 ml/hour and the eluate collected in fractions. Each fraction was examined using HPLC for the presence of the syn and anti isomers. The early eluate fractions were combined together (total volume 610 ml); methyl acetate (750 ml) and sodium chloride (120 g) were added with stirring. Whilst continuing stirring, 15% v/v sulphuric acid was added to pH 2.0. After stirring for 10 minutes at pH 2.0, the lower aqueous phase was separated and extracted with a second portion of methyl acetate (100 ml). The methyl acetate fractions were combined and sodium 2-ethylhexanoate solution was added to pH 5.5. The resultant slurry was filtered. The filter cake was washed with methyl acetate and dried overnight in vacuo at 40°. The dry product (23.99 g) was found to contain 21.9 g of sodium (6R,7R)-3-carbamoyloxymethyl-7-[2-(fur-2-yl)-2-methoxyiminoacetamido]ceph-3-em-4-carboxylate, syn isomer and 0.41 g of the corresponding anti isomer.

EXAMPLE 4

Separation of Isomers of sodium (6R,7R)-3-carbamoyloxy-methyl-7-[2-(fur-2-yl)-2-methoxyimino-acetamido]ceph-3-em-4-carboxylate A mixture of sodium (6R,7R)-3-carbamoyloxymethyl-7-[2-(fur-2-yl)-2-methoxyiminoacetamido]ceph-3-em-4-carboxylate, syn-isomer (27.59 g) and the corresponding anti-isomer (5.38 g) as the tetrahydrofuran solvate was dissolved in water (300 ml). The solution was loaded at 250 ml/hour to a column containing Mitsubishi SP 207 resin (250 ml). All the cephalosporin was retained on the resin, none being detected in the percolate, which was discarded. The resin was eluted with water at 250 ml/hour and the eluate collected in fractions. Each fraction was examined using HPLC for the presence of the syn and anti-isomers. The early eluate fractions were combined together (total volume 400 ml); methyl acetate (750 ml) and sodium chloride (80 g)

were added with stirring. Whilst continuing stirring, 15% v/v sulphuric acid was added to pH 2.0. After stirring for 10 minutes at pH 2.0, the lower aqueous phase was separated and extracted with a second portion of methyl acetate (100 ml). The methyl acetate fractions were combined and sodium 2-ethyl hexanoate solution was added to pH 5.5. The resultant slurry was filtered, washed with methyl acetate and dried overnight in vacuo at 40° C. The dry product (20.24 g) was found to contain 18.09 g of sodium (6R,7R)-3-carbamoyloxymethyl-7-[2-(fur-2-yl)-2-methoxyimino-acetamido]ceph-3-em-4-carboxylate, syn-isomer and 0.43 g of the corresponding anti-isomer.

EXAMPLE 5

Separation of Isomers of sodium (6R,7R)-7-[2-(fur-2-yl)-2-methoxyimino-acetamido]-3-acetoxymethylceph-3-em-4-carboxylate A mixture of sodium (6R,7R)-3-acetoxymethyl-7-[2-(fur-2-yl)-2-methoxyimino-acetamido]ceph-3-em-4-carboxylate, syn-isomer (added as the dioxan solvate) (21.9 g) and the corresponding anti-isomer (3.2 g) was prepared in water (250 ml) at pH 6.0. The solution was loaded at 1,000 ml/hour to a column containing Rohm and Haas XAD 1180 resin (500 ml). All of the cephalosporin was retained on the resin, none being detected in the percolate, which was discarded. The resin was eluted with water at 1,000 ml/hour and the eluate collected in fractions. Each fraction was examined using HPLC for the presence of the syn and anti isomers. The early eluate fractions were combined together (total volume 1,735 ml) and found to contain 17.5 g of the syn isomer and 0.2 g of the anti isomer. This fraction (1684 ml) was concentrated in vacuo to give a solution that was about 10% w/v cephalosporin compound.

The concentrated solution (10 w/v) was extracted into dichloromethane (2×150 mls) at pH 2.0. The organic extract was then evaporated to a solid which was redissolved using IMS (180 mls).

A solution of sodium 2-ethyl hexanoate (8.4 g) was added to the solution of cephalosporin acid and the mixture was stirred for 18 hours. The solid was filtered, washed with IMS, and dried in vacuo at 40° C. The dried solution (75.7% yield from the aqueous column eluate) was pure sodium (6R,7R)-7-[2-(fur-2-yl)-2-methoxyiminoacetamido]-3-acetoxymethylceph-3-em-4-carboxylate syn isomer containing 0.7% w/w anti isomer.

EXAMPLE 6

Separation of Isomers of Sodium (6R, 7R)-7-[2-(fur-2-yl)-2-methoxyiminoacetamido]-3-acetoxymethylceph-3-em-4-carboxylate A mixture of sodium (6R, 7R)-3-acetoxymethyl-7-[2-(fur-2-yl)-2-methoxyiminoacetamido]ceph-3-em-4-carboxylate syn isomer (added as the dioxan solvate) (21.9 g) and the corresponding anti-isomer (3.2 g) was prepared in water (250 ml) at pH 6.0. The solution was loaded at 1,000 ml/hour to a column containing Rohm and Haas XAD 1180 resin (500 ml). All of the cephalosporin was retained on the resin, none being detected in the percolate, which was discarded. The resin was eluted with 6% v/w methanol water at 1,000 ml/hr and the eluate collected in fractions. Each fraction was examined using HPLC for the presence of the syn and anti isomers. The early eluate fractions were combined together (total volume 1480 ml) and found to contain 18.2 g of the syn isomer and 0.2 g of the anti isomer.

This fraction (1428 ml) was concentrated in vacuo to give a solution that was about 10% w/v cephalosporin compound.

The concentrated solution (10 w/v) was extracted into dichloromethane (2×150 mls) at pH 2.0. The organic extract was then evaporated to a solid which was redissolved using IMS (180 mls).

A solution of sodium 2-ethyl hexanoate (8.4 g) was added to the solution of cephalosporin acid and the mixture was stirred for 18 hours. The solid was filtered, washed with IMS, and dried in vacuo at 40° C. The dried solution (79.3% yield from the aqueous column eluate) was pure sodium (6R,7R)-7-[2-(fur-2-yl)-2-methoxyiminoacetamido]-3-acetoxymethylceph-3-em-4-carboxylate syn isomer containing 1.0% w/w anti isomer.

EXAMPLE 7

Separation of Isomers of (6R, 7R)-7-2-(2-aminothiazol-4-yl)-2-(2-carboxyprop-2-oxyimino) acetamido-3-(1-pyridiniummethyl)ceph-3-em-4-carboxylate A mixture of (6R, 7R)-[2-(2-aminothiazol-4-yl)-2-(2-carboxyprop-2-oxyimino)acetamido]-3-(1-pyridiniummethyl)ceph-3-em-4-carboxylate, syn isomer (21.1 g) and the corresponding anti isomer (0.8 g) was dissolved in water (250 ml) at pH 6.0. The solution was loaded at 500 ml/hour to a column containing Rohm and Haas XAD 1180 resin (500 ml). All the cephalosporin was retained on the resin, none being detected in the percolate, which was discarded. The resin was eluted with water at 500 ml/hour and the eluate collected in fractions. Each fraction was examined using HPLC for the presence of syn and anti isomers. The early eluate fractions were combined together (total volume 590 ml) and contained 81.7% of the input syn isomer. A portion of the eluate (500 ml) was adjusted to pH 6.0 with phsophoric acid and freeze-dried to a solid of 99.8% syn, 0.2% anti geometric isomer composition.

EXAMPLE 8

Separation of Isomers of 2-(Fur-2-yl)-2-methoxyiminoacetic acid

A mixture of ammonium 2-(fur-2-yl)-2-methoxyiminoacetate, syn isomer (5.50 g) and 2-(fur-2-yl)-2-methoxyiminoacetic acid, anti isomer (0.50 g) were dissolved in water and the pH of the solution adjusted to 3.0 to give 81 ml of solution. This solution was passed at 100 ml/hour down a column containing Amberlite XAD-1180 resin (100 ml). The column was then eluted with water at 100 ml/hour. The eluate from the column was collected in fractions and each fraction examined using HPLC for the presence of the syn and anti isomers. The early eluate fractions (183 ml) contained 82% of the syn isomer originally present (contaminated with 3% of anti isomer). The 2-(fur-2-yl)-2-methoxyiminoacetic acid syn isomer was recovered from these early fractions by extraction into dichloromethane at pH 0.2. Evaporation of the dried organic extract yielded a solid which was contaminated with 2% of the anti isomer.

EXAMPLE 9

Separation of Isomers of (6R, 7R)-7-(2-aminothiazol-4-yl)-2-cyclopropylmethoxyiminoacetamido]-3-(1-pyridiniummethyl)ceph-3-em-4-carboxylate A mixture of (6R, 7R)-[2-(2-aminothiazol-4-yl)-2-cyclopropylmethoxyiminoacetamido]-3-(1-pyridiniummethyl)-ceph-3-em-4-carboxylate syn isomer (added as the bis-ethylene glycol solvate) (9.07 g) and the corresponding anti isomer (1.56 g) was prepared in water (102 ml) at pH 4.2. The solution was loaded at 200 ml/hour to a column containing Rohm and Hass XAD 1180 resin (200 ml). All of the cephalosporin was retained on the resin, none being detected in the percolate, which was discarded. The resin was washed with water (200 ml) at 200 ml/hour and then eluted with 30% methanol-water at 200 ml/hour and the eluate collected in fractions. Each fraction was examined using HPLC for the presence of the syn and anti isomers. The early eluate fractions were combined together (total volume 450 ml) and found to contain 7.37 g of the syn isomer and no anti isomer. This bulked fraction was evaporated in vacuo to remove methanol and freeze-dried to a solid that contained no anti isomer.

EXAMPLE 10

Separation of Isomers of (R,S)-1-Acetoxyethyl3-carbamoyloxymethyl-7-[2-(fur-2-yl)-2-methoxyiminoacetamido]-ceph-3-em-4-carboxylate A mixture of (R,S)-1-acetoxyethyl3-carbamoyloxymethyl-7-[2-(fur-2-yl)-2-methoxyiminoacetamido]-ceph-3-em-4-carboxylate syn isomer (20.13 g) and the corresponding anti isomer (1.08 g) was prepared in N,N-dimethylacetamide (40 ml). The solution was loaded at 500 ml/hr to a column containing Rohm and Haas XAD 1180 resin (500 ml). Water (750 ml) was passed down the column at 500 ml/hr to remove the N,N-dimethylacetamide. All the cephalosporin was retained on the column, none being detected in the percolate, which was discarded. The resin was eluted with 60% v/v methanol/water at 500 ml/hour and the eluate collected in fractions. Each fraction was examined using HPLC for the presence of syn and anti isomers. Fractions totalling 1,800 ml rich in syn isomer were combined and evaporated in vacuo to a volume of 500 ml. This was then extracted twice with ethyl acetate (1×250 ml, 1×100 ml). The combined ethyl acetate extracts were evaporated to 100 ml in vacuo and the concentrate seeded and stirred vigorously for 30 minutes. IMS (90 ml) was added followed by demineralised water (180 ml) and the mixture concentrated in vacuo to 240 ml. The suspension was stirred at 25° C. for 30 minutes before filtering off the solid and washing with a mixture of water (117 ml) and IMS (17 ml). The product was dried in vacuo at 60° C. The solid was found to contain 6.16 g (R,S)-1-acetoxylethyl3-carbamoyloxymethyl-7-[2-(fur-2-yl)-2-methoxyiminoacetamido]-ceph-3-em-4-carboxylate syn isomer and none of the corresponding anti isomer.

EXAMPLE 11

Separation of Isomers of (R,S)-1-acetoxyethyl 3-carbamoyloxymethyl-7-[2-(fur-2-yl)-2-methoxyiminoacetamido]-ceph-3-em-4-carboxylate A mixture of (R,S)-1-acetoxyethyl 3-carbamoyloxymethyl-7-[2-(fur-2-yl)-2-methoxyiminoacetamido]-ceph-3-em-4-carboxylate syn isomer (20.93 g) and the corresponding anti isomer (2.15 g) was prepared in N,N-dimethylacetamide (40 ml). The solution was loaded at 500 ml/hour to a column containing Rohm and Haas XAD 1180 resin (500 ml). Water (750 ml) was passed down the column at 500 ml/hr to remove the N,N-dimethylacetamide. All the cephalosporin was retained on the column, none being detected in the percolate, which was discarded. The resin was eluted with 60% v/v methanol water at 500 ml/hr and the eluate collected in fractions.

Each fraction was examed using HPLC for the presence of syn and anti isomers. Fraction rich in syn isomer totalling 1,700 ml were combined and evaporated in vacuo to a volume of 500 ml. This was then extracted twice with ethyl acetate (1×250 ml, 1×100 ml). The combined ethyl acetate extracts were evaporated to 100 ml in vacuo and the concentrate seeded and stirred vogorously for 1 hour. The resulting suspension was stored overnight. IMS (90 ml) was added followed by water (180 ml) and the mixture concentrated in vacuo to 240 ml. The suspension was stirred at 25° C. for 30 minutes before filtering off the solid and washing with a mixture of water (117 ml) and IMS (17 ml). The product was dried in vacuo at 60° C. The solid was found to contain 8.50 g (R,S)-1-acetoxyethyl 3-carbamoyloxymethyl-7-[2-(fur-2-yl)-2-methoxyiminoacetamido]-ceph-3-em-4-carboxylate syn isomer and the corresponding anti isomer (0.16 g).

EXAMPLE 12

Separation of isomers of (6R,7R)-7-[2-(2-aminothiazol-4-yl)-2-cyclopropylmethoxyiminoacetamido]-3-(1-pyridiniummethyl)-ceph-3-em-4-carboxylate A mixture of (6R,7R)-7-[2-(2-aminothiazol-4-yl)-2-cyclopropylmethoxyiminoacetamido]-3-(1-pyridiniummethyl)-ceph-3-em-4-carboxylate, syn isomer (added as the bis-ethylene glycol solvate) (9.22 g) and the corresponding anti isomer (1.29 g) was prepared in water (104 ml) at pH 4.1. The solution was loaded at 200 ml/hr to a column containing Rohm and Haas XAD 7 resin (200 ml). All the cephalosporin was retained on the resin, none being detected in the percolate, which was discarded. The resin was eluted with water at 200 ml/hr and the eluate collected in fractions. Additional fractions were also collected using 10% v/v methanol-water eluant at a rate of 400 ml/hr. Each fraction was examined using HPLC for the presence of syn and anti isomers. The eluate fractions were combined together (total volume 1364 ml) and found to contain 6.28 g of the desired syn isomer and no detected anti isomer.

EXAMPLE 13

Separation of isomers of sodium (6R,7R)-7-[2-(2-aminothiazol-4-yl)-2-methoxyiminoacetamido]-3-acetoxymethylceph-3-em-4-carboxylate A mixture of sodium (6R,7R)-7-[2-(2-aminothiazol-4-yl)-2-methoxyiminoacetamido]-3-acetoxymethylceph-3-em-4-carboxylate syn isomer (5.15 g) and the corresponding anti isomer (0.40 g) was prepared in water (106 ml) at pH 5.5. The solution was loaded at 240 ml/hr to a column containing Rohm and Haas XAD 1180 resin (120 ml). All of the cephalosporin was retained on the resin, none being detected in the percolate, which was discarded. The resin was eluted with water at 240 ml/hr and the eluate collected in fractions. Each fraction was examined using HPLC for the presence of syn and anti isomers. The early eluate fractions were combined together (total volume 420 ml) and found to contain 4.44 g of the syn isomer and not more than 0.02 g of the anti isomer.

EXAMPLE 14

Separation of isomers of sodium (6R,7R)-7-[2-(2-aminothiazol-4-yl)-2-methoxyiminoacetamido]ceph-3-em-4-carboxylate A mixture of sodium (6R,7R)-7-[2-(2-aminothiazol-4-yl)-2-methoxyiminoacetamido]ceph-3-em-4-carboxylate syn isomer (5.73 g) and the corresponding anti isomer (0.28 g) was prepared in water (153 ml) at pH 6.0. The solution was loaded at 240 ml/hr to a column containing Rohm and Haas XAD 1180 resin (120 ml). All the cephalosporin was retained on the resin, none being detected in the percolate which was discarded. The resin was eluted with water at 240 ml/hr and the eluate collected in fractions. Each fraction was examined, using HPLC, for the presence of the syn and anti isomers. The early eluate fractions were combined together (total volume 360 ml) and found to contain 5.69 g of syn isomer and no detected anti isomer.

We claim:

1. A process for separating a mixture of syn and anti oxime isomers, one from the other, of a water-soluble cephalosporin compound of formula

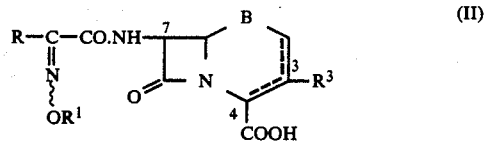

(II)

wherein each of R, $R^1$ and $R^3$ independently represents an organic group and $R^3$ may additionally represent a hydrogen atom; B is —S— or >S→O ($\alpha$- or $\beta$-) and the dotted line indicates $\Delta^2$ or $\Delta^3$ unsaturation; or an ester, salt or solvate thereof; which comprises adsorbing said mixture of oxime isomers onto a non-functional macroreticular adsorption resin, and eluting said resin to yield at least one eluate fraction containing one of said isomers substantially free of the other of said isomers.

2. A process as claimed in claim 1 wherein R is a carbocyclic group or heterocyclic group, said groups being unsaturated or aromatic and any heterocyclic group having 5 or 6 ring members and containing from 1 to 4 heteroatoms selected from the group consisting of sulphur, nitrogen, and oxygen; said groups optionally being substituted; or R is an optionally substituted $C_{1-6}$ alkyl group.

3. A process as claimed in claim 2 wherein $R^1$ represents $C_{5-10}$ aryl or $C_{5-10}$ aralkyl group or an aliphatic group which is $C_{1-6}$ alkyl, $C_{3-7}$ cycloalkyl, $C_{4-10}$ cycloalkylalkyl, $C_{2-6}$ alkenyl or $C_{4-7}$ cycloalkenyl, or one of these groups substituted by a free or blocked carboxy, carbamoyl, cyano or protected or unprotected amino group.

4. A process as claimed in claim 2 wherein $R^3$ represents a hydrogen atom; a vinyl group substituted by a heterocyclicthio group in which the heterocyclic portion is a 5- or 6-membered ring containing up to four nitrogen atoms and optionally one sulphur atom and substituted by one or more groups which may be methyl, protected or unprotected oxo, formylmethyl, protected or unprotected hydroxy, free or blocked carboxymethyl groups; or a group of formula

—CH$_2$Y wherein Y represents a halogen atom, a hydroxy, acyloxy or carbamoyloxy group or the residue of pyridine, 2,3-cyclopentenopyridine, nicotinamide, or isonicotinamide or of a heterocyclicthiol comprising a 5- or 6-membered heterocyclic portion containing up to four nitrogen atoms and optionally one sulphur atom and substituted by one or more groups independently selected from methyl, protected or unprotected oxo, formylmethyl, carbamoylmethyl protected or unprotected hydroxy and free or blocked carboxymethyl groups.

5. A process as claimed in claim 3 wherein $R^3$ represents a hydrogen atom; a vinyl group substituted by a heterocyclicthio group in which the heterocyclic portion is a 5- or 6-membered ring containing up to four nitrogen atoms and optionally one sulphur atom and substituted by one or more groups which may be methyl, protected or unprotected oxo, formylmethyl, protected or unprotected hydroxy, free or blocked carboxymethyl groups; or a group of formula

—CH$_2$Y wherein Y represents a halogen atom, a hydroxy, acyloxy or carbamoyloxy group or the residue of pyridine, 2,3-cyclopentenopyridine, nicotinamide, or isonicotinamide or of a heterocyclicthiol comprising a 5- or 6-membered heterocyclic portion containing up to four nitrogen atoms and optionally one sulphur atom and substituted by one or more groups independently selected from methyl, protected or unprotected oxo, formylmethyl, carbamoylmethyl protected or unprotected hydroxy and free or blocked carboxymethyl groups.

6. A process as claimed in claim 1 wherein the compound of formula (II) is cefuroxime or its 3-acetoxymethyl and 3-hydroxymethyl analogues; ceftazidime: ceftizoxime; ceftriaxone; cefotaxime; cefmenoxime; cefodizime; cefpirome; (6R,7R)-7-[(Z)-2-(2-aminothiazol-4-yl)-2-methoxyiminoacetamido]-3-[2-(5,6-dioxo-4formylmethyl-1,4,5,6-tetrahydro1,2,4-triazin-3-yl)thiovinyl]ceph-3-em-4-carboxylic acid; (6R,7R)-7-[(Z)-2-(2-aminothiazol-4-yl)-2-(caraboxymethoxyimino)acetamido]-3-vinyl-ceph-3 -em-4-carboxylic acid; (6R,7R)-7-[(Z)-2-(2-aminothiazol-4-yl)-2cyclopropylmethoxyiminoacetamido]-3-pyridinium-methylceph-3-em-4-carboxylate; or (6R,7R)-7-[(Z)-2-(2-aminothiazol-4-yl)-2-methoxyiminoacetamido]-3-[(1-methyl-1-pyrrolidinium)methyl]-ceph-3-em4-carboxylate.

7. A process as claimed in claim 1 wherein the nonfunctional macroreticular resin is a copolymer of styrene cross-linked with divinyl benzene or an acrylic ester polymer.

8. A process as claimed in claim 2 wherein the nonfunctional macroreticular resin is a copolymer of styrene cross-linked with divinyl benzene or an acrylic ester polymer.

9. A process as claimed in claim 3 wherein the nonfunctional macroreticular resin is a copolymer of styrene cross-linked with divinyl benzene or an acrylic ester polymer.

10. A process as claimed in claim 4 wherein the nonfunctional macroreticular resin is a copolymer of styrene cross-linked with divinyl benzene or an acrylic ester polymer.

11. A process as claimed in claim 5 wherein the nonfunctional macroreticular resin is a copolymer of styrene cross-linked with divinyl benzene or an acrylic ester polymer.

12. A process as claimed in claim 6 wherein the nonfunctional macroreticular resin is a copolymer of styrene cross-linked with divinyl benzene or an acrylic ester polymer.

13. A process as claimed in claim 1 wherein the oxime isomers are soluble in aqueous media and elution is effected using an aqueous eluant.

14. A process as claimed in claim 2 wherein the oxime isomers are soluble in aqueous media and elution is effected using an aqueous eluant.

15. A process as claimed in claim 3 wherein the oxime isomers are soluble in aqueous media and elutin is effected using an aqueous eluant.

16. A process as claimed in claim 4 wherein the oxime isomers are soluble in aqueous media and elution is effected using an aqueous eluant.

17. A process as claimed in claim 5 wherein the oxime isomers are soluble in aqueous media and elution is effected using an aqueous eluant.

18. A process as claimed in claim 6 wherein the oxime isomers are soluble in aqueous media and elution is effected using an aqueous eluant.

19. A process as claimed in claim 18 wherein the oxime isomers are soluble in aqueous media and elution is effected using an aqueous eluant.

20. A process as claimed in claim 8 wherein the oxime isomers are soluble in aqueous media and elution is effected using an aqueous eluant.

* * * * *